US009781907B2

(12) United States Patent
Garcia et al.

(10) Patent No.: US 9,781,907 B2
(45) Date of Patent: Oct. 10, 2017

(54) SYSTEM TO DETECT THE LEVEL OF STRESS/DISCOMFORT OF AQUATIC ANIMALS

(75) Inventors: Gonzalo A Garcia, San Sebastian (ES); Sandra Rainieri, Sukarrieta (ES)

(73) Assignee: FUNDACION AZTI, Sukarrieta (ES)

( * ) Notice: Subject to any disclaimer, the term of this patent is extended or adjusted under 35 U.S.C. 154(b) by 178 days.

(21) Appl. No.: 14/375,057

(22) PCT Filed: Jan. 27, 2012

(86) PCT No.: PCT/EP2012/051317
§ 371 (c)(1),
(2), (4) Date: Jul. 28, 2014

(87) PCT Pub. No.: WO2013/110342
PCT Pub. Date: Aug. 1, 2013

(65) Prior Publication Data
US 2014/0375298 A1    Dec. 25, 2014

(51) Int. Cl.
*G01N 27/00* (2006.01)
*A01K 61/00* (2017.01)
(Continued)

(52) U.S. Cl.
CPC .............. *A01K 61/00* (2013.01); *A01K 29/00* (2013.01); *A01K 29/005* (2013.01); *A01K 63/00* (2013.01);
(Continued)

(58) Field of Classification Search
CPC ...... A01K 31/00; A01K 29/00; A01K 29/005; A01K 63/00; A01K 63/006; A01K 61/00;
(Continued)

(56) References Cited

U.S. PATENT DOCUMENTS 4,723,511 A * 2/1988 Solman ................ G01N 33/186
119/200
5,307,052 A   4/1994 Harrison et al.
(Continued)

FOREIGN PATENT DOCUMENTS

JP        9178731 A    7/1997
JP     2002085362 A    3/2002
(Continued)

OTHER PUBLICATIONS

International Preliminary Report and Written Opinion by European Patent Office (EPO) on May 22, 2014.

*Primary Examiner* — Arleen M Vazquez
*Assistant Examiner* — Steven Yeninas
(74) *Attorney, Agent, or Firm* — Michael B. Fein; Eckert Seamans Cherin & Mellott, LLC (57) ABSTRACT

System for detecting the level of discomfort of aquatic animals during experimental studies, with a water tank, a reference electrode placed at one of the sides of the tank, at least one recording electrode placed at another side of the tank, a bio amplifier for amplifying a received bio-signal at the recording electrode, a microprocessor for treating the signals and a low-pass filter for filtering the signals received. The system can provide a precise, quantifiable and specific indication of the level of stress/wellbeing of aquatic animals in normal living conditions as well as in experimental conditions without interfering with the animals' life.

4 Claims, 7 Drawing Sheets

(51) Int. Cl.
*A01K 29/00* (2006.01)
*A61B 5/00* (2006.01)
*A61B 5/04* (2006.01)
*A61B 5/11* (2006.01)
*A61B 5/16* (2006.01)
*G01N 33/18* (2006.01)
*A01K 63/00* (2017.01)
*A61D 99/00* (2006.01)
*A01K 61/10* (2017.01)

(52) U.S. Cl.
CPC ........ *A01K 63/006* (2013.01); *A61B 5/04004* (2013.01); *A61B 5/1105* (2013.01); *A61B 5/165* (2013.01); *A61B 5/6887* (2013.01); *A61D 99/00* (2013.01); *G01N 33/186* (2013.01); *A01K 61/10* (2017.01); *A61B 2562/0209* (2013.01)

(58) Field of Classification Search
CPC .. A01K 61/008; A01K 63/003; A61B 5/0006; A61B 5/04004; A61B 5/1105; A61B 5/165; A61B 5/6887; A61D 99/00; G01N 33/18; G01N 33/186; G01N 33/1886
USPC ... 324/71.1, 76.39, 691, 692, 693, 753, 754, 324/762, 782; 340/573.2, 573.3, 573, 340/753, 754, 762, 782; 73/215, 224, 73/225, 227, 259, 260, 53.01, 304 R, 73/61.41, 61.43, 61.61, 304 C; 119/51.04, 224, 225, 226, 227, 228, 231, 119/245, 259, 260, 269; 364/413.03
See application file for complete search history.

(56) References Cited

U.S. PATENT DOCUMENTS

| 6,084,392 | A | * | 7/2000 | Shine ................. G01N 15/1218 |
| | | | | 204/409 |
| 6,393,899 | B1 | | 5/2002 | Shedd et al. |
| 2005/0253601 | A1 | * | 11/2005 | Kittrell .................. G01N 27/06 |
| | | | | 324/696 |
| 2013/0146683 | A1 | * | 6/2013 | Imai ........................ B05B 5/057 |
| | | | | 239/690 |

FOREIGN PATENT DOCUMENTS

| JP | 2007064783 A | 3/2007 |
| JP | 2010223590 A | 10/2010 |
| WO | WO 9944057 A1 | 9/1999 |
| WO | WO 2009089339 A2 | 7/2009 |

* cited by examiner

SYSTEM TO DETECT THE LEVEL OF STRESS/DISCOMFORT OF AQUATIC ANIMALS

FIELD OF THE INVENTION

The present invention relates to a system for biomonitoring; namely, for detecting the level of stress or discomfort that aquatic animals such as fish or frogs undergo while experimental studies are carried out with them and also during their normal living conditions while maintained in laboratory tanks, in private houses as a hobby, in restaurants for exhibition of aquatic animals such as fish or seafood to costumers, in aquaculture centres for fish production, etc. In particular, the system is of the type comprising a water tank and an array of electrodes employed for recording electromyographic (EMG) and other biological signals produced by the activity of the aquatic animals present in the tank.

STATE OF THE ART

Aquatic animals such as fish and frogs are widely known animal models that are extensively used in medicine (to study diseases), pharmacology (to test new drugs), ecotoxicology (to test vertebrate responses to pollutants), etc. Results of in vivo experiments carried out with aquatic animals can be affected by several factors. Stress plays the major role with this respect. Fertility and response to treatment, for example, are greatly affected by stressful conditions. A rational, quantitative measure of the level of stress during aquatic animal-based experimentation is thus needed. Ignoring this factor could lead to the misinterpretation of the final results of in vivo experiments.

The use of biological signals for detecting the motor activity of aquatic animals has been applied in devices directed to the use of aquatic animals as eco-toxicological sensors for determining the quality of water. The device described in patent U.S. Pat. No. 5,307,052, converts the ventilatory behaviour of fish into a signal and considers the signal an instantaneous and direct determination of the quality of the water being tested. The system is based on the amplification, filtration and elaboration of electrical signals obtained from fish placed individually in a series of water tanks of a size similar to that of the fish, containing the water to be tested and two electrodes placed inside the tank to acquire the signals.

The device described in patent application JP2002085362 measures the bio-potentials (i.e. electrical signals of biological origin) of aquatic organisms through electrodes placed in the centre of the water tank. In this application the authors claim that the device can measure bio-potentials of aquatic organisms in their living conditions.

In both the abovementioned cases (U.S. Pat. No. 5,307,052 and JP2002085362), the electrodes are placed in the middle of the water tank and this interferes with the free movement of the animals, thus altering their normal living conditions and movement patterns. Moreover, the signals produced can be detected only if the animal is positioned in the space between the two electrodes. Being these placed in the middle of the tank it is obvious that if the animal moves in a part of the tank not included between the electrodes, no signal will be detected. In other words, the abovementioned systems do not allow the monitoring of the signals produced by the animals in their normal living conditions, with the exception of when they find themselves between the two electrodes.

Patent application WO9944057 describes an analogous device in which bio-potentials are measured by disposing a reference electrode plate at the bottom of the tank and a second electrode plate floating on the surface of the water. In this way the authors claim to allow the animal free motility, diminishing animal stress and facilitating the cleaning and maintenance of the system. The problem that this system might cause is due to the fact that a floating superficial electrode plate might move with the natural movement of the water and, even if very slight, this movement will distort the detected signal produced by the animals. Moreover, the presence of an upper plate covering the entire water tank surface blocks the entrance of light that is necessary for the normal living conditions of aquatic animals.

In U.S. Pat. No. 6,273,026, the electrodes are placed in a water tank and a current is applied between them, the variation of the waveform providing an indication of the animal's behaviour. Even though this might work for specific behavioural tests, the system is not suitable for testing the level of stress/wellbeing of aquatic animals, since the application of a current through the electrodes will be strongly perceived by the animals and will cause heavy conditions of stress altering their normal living conditions.

Therefore, the existing solutions use electrodes that disturb and negatively condition the status and behaviour of the aquatic animals under study. Furthermore, the devices of the prior art are designed for testing one animal at a time, whereas aquatic animals are generally gregarious and live in groups. Also, none of the devices of the prior art takes into account the mere presence of water in the quality of the recordings, the background electromagnetic noise, neither is able to distinguish it from the real signals.

SUMMARY OF THE INVENTION

The present invention solves the problems exposed above by providing a device able to measure quantitatively the level of stress in aquatic animals; establishing a whole measuring system and facilitating the development of a specific "stress scale" to be introduced routinely in fish-based experiments. This is achieved by:
  New types of electrodes and optimal electrodes arrangements for the sensing of the bio-signals.
  Filtering of the obtained signals to reduce the level of electromagnetic noise on them.
  Means for the processing and interpretation of the bio-signals.

The invention comprises a water tank, an array of electrodes employed for recording electromyographic (EMG) or other biological signals produced by the activity of aquatic animals present in the tank, a bio-amplifier for signal amplification, a micro-processor and a low pass filter.

The reference and signal electrodes can be made of the same material, preferably aluminum, copper or silver. The electrodes can be embedded in the walls of the tank or supported on sheets attached to the sides of the tank. The low-pass filter is preferably capable of filtering signals up to 20 Hz.

BRIEF DESCRIPTION OF THE DRAWINGS

To complete the description and in order to provide for a better understanding of the invention, a set of drawings is provided. Said drawings illustrate a preferred embodiment of the invention, which should not be interpreted as restricting the scope of the invention, but just as an example of how the invention can be embodied.

DESCRIPTION OF THE INVENTION

Figure 1:
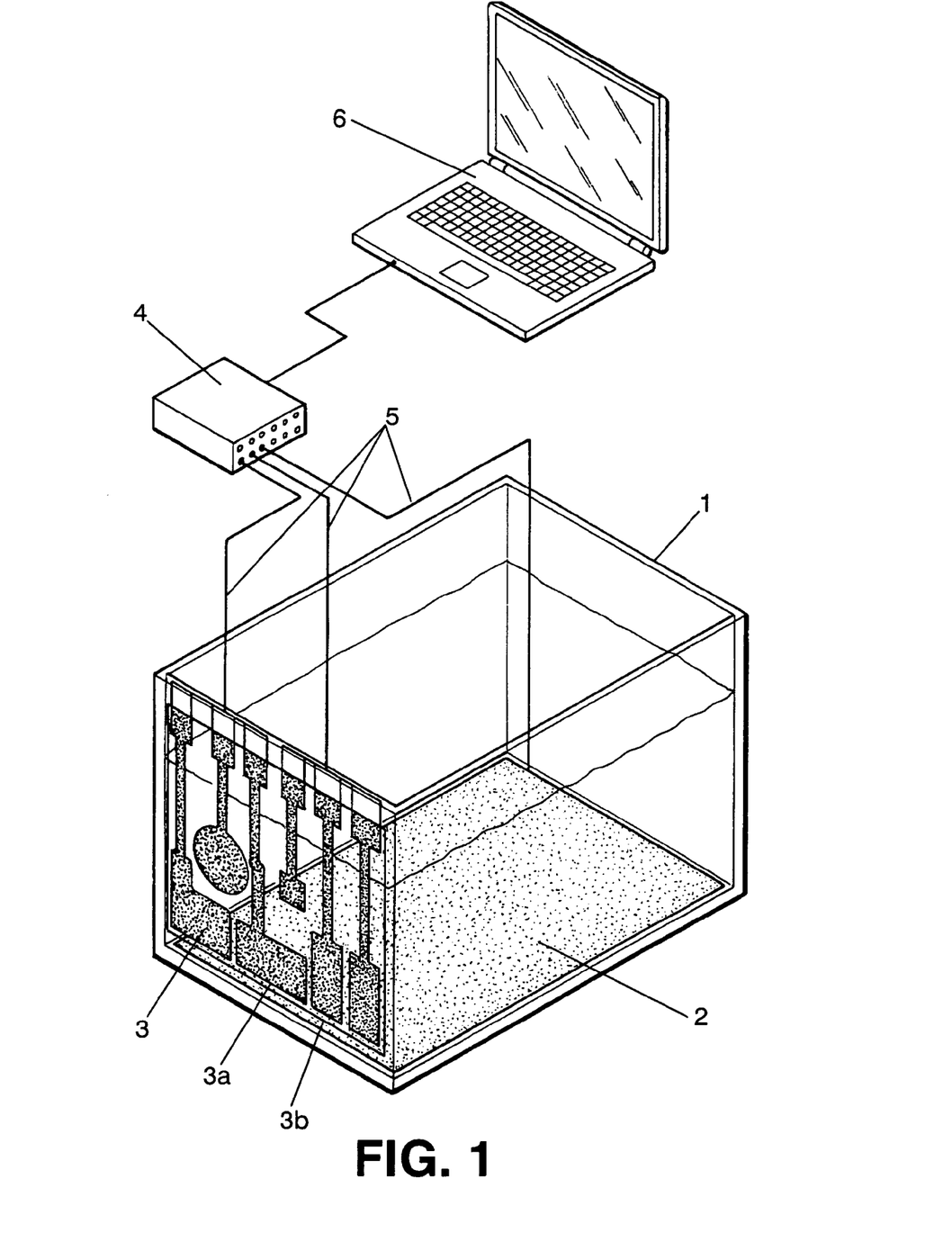
FIG. 1 is a schematic representation of the device of the invention.

With reference to FIG. 1, the invention comprises a reference electrode (2). placed in one of the sides of the water tank (1) so as to cover its entire surface. By side it is meant any of the walls of the tank, including also its bottom. At least one array of recording electrodes, acquiring the biological signals produced by the animals is placed in at least one of the other sides of the tank. The recording electrodes (3 a, 3 b, . . . ) are coupled to a bio-amplifier (4) through cables (5). The signals so amplified are passed to a micro-processor in a computer (6) that is in charge of filtering and interpreting them.

Reference Electrode

As any electronic system, the present invention needs an electrode to be used as voltage reference. This electrode is called reference or ground electrode. The bigger it is the reference electrode, the clearer and more stable signals will be obtained. Therefore, the ideal situation is when this electrode is as big as one of the sides of the tank (including its bottom), assuming a square type of tank. In a circular type, the electrode could be put in its bottom or—curving it—occupying half of the cylinder.

There are two main ways of acquiring a signal: monopolarly or bipolarly. In the monopolar case, the measurement is made between an electrode and a reference electrode. In the bipolar case, the measurement is done between two similar electrodes (in this case, also a reference electrode is needed anyway to provide a fix, stable reference).

The position of the recording electrode array with respect to the reference electrode greatly influences the detection of the signal. The larger the distance between the recording array with respect to the reference electrode is, the bigger is the amplitude of the signal detected. For example, in the case of stainless steal, that relationship is almost lineal ($R^2>0.95$); that is, the amplitude of the registered signal increases 2 times if the electrode gets a double distance farther from the reference electrode.

Array of Recording Electrodes

Due to the extremely low amplitude of the bio-potential signals produced by aquatic animals, the original recordings must be of superior quality to allow a correct interpretation of the signals. In the present invention specific electrodes and electrodes setups have been developed to achieve this. Their characteristics are described as follows.

Material: Copper, Silver, and Aluminium have experimentally shown to be the most appropriate materials for the construction of the electrodes. Specifically, these metals have a high conductivity, a high Signal-to-Noise Ratio (SNR), they do not oxidize, their performance is not affected by acidic environment, and their electrical behaviour is independent form the frequency of the signal. All these characteristics are essential to allow the electrode to detect the very low signals from the biological activity of aquatic animals, and to do so in a reliable and robust way in spite of the harsh environment.

Under a biological point of view, the electrodes constructed with those materials and setups in the way they are in the presented device are not toxic for animal life, they do not release ions in the aquatic media, and are visually irrelevant for the animals: not causing any visual stress or restriction in animal movements. These metals can be easily cut into singular plaques acting as electrodes, or embedded into other support materials such as plastic in order to create easily portable sheets, or even to be embedded into the walls of the aquaria. They can also be obtained using the habitual technical process of printed circuit boards (PCBs), which allows the design of very effective electrodes that can be designed to cover the entire surface of one of the sides of the water tank, optimizing the signal acquisition and at the same time allowing easy transport and replacement. A similar technique (thin-film fabrication) can be used to create flexible electrodes, by printing them directly on a thin plastic sheet.

The electrodes can also be made with high-quality wires peeled off of their plastic shield, so that the internal fine wires are exposed to the water.

The electrodes need not to be planar; they can be, for example, spherical. In that case, rather than placing them embedded into the walls, several of them could be placed hanging on a spider-like structure so that they can be inserted at the same time into the tank, remaining close to the walls to avoid disturbances to the animals in the tank.

Figure 4:
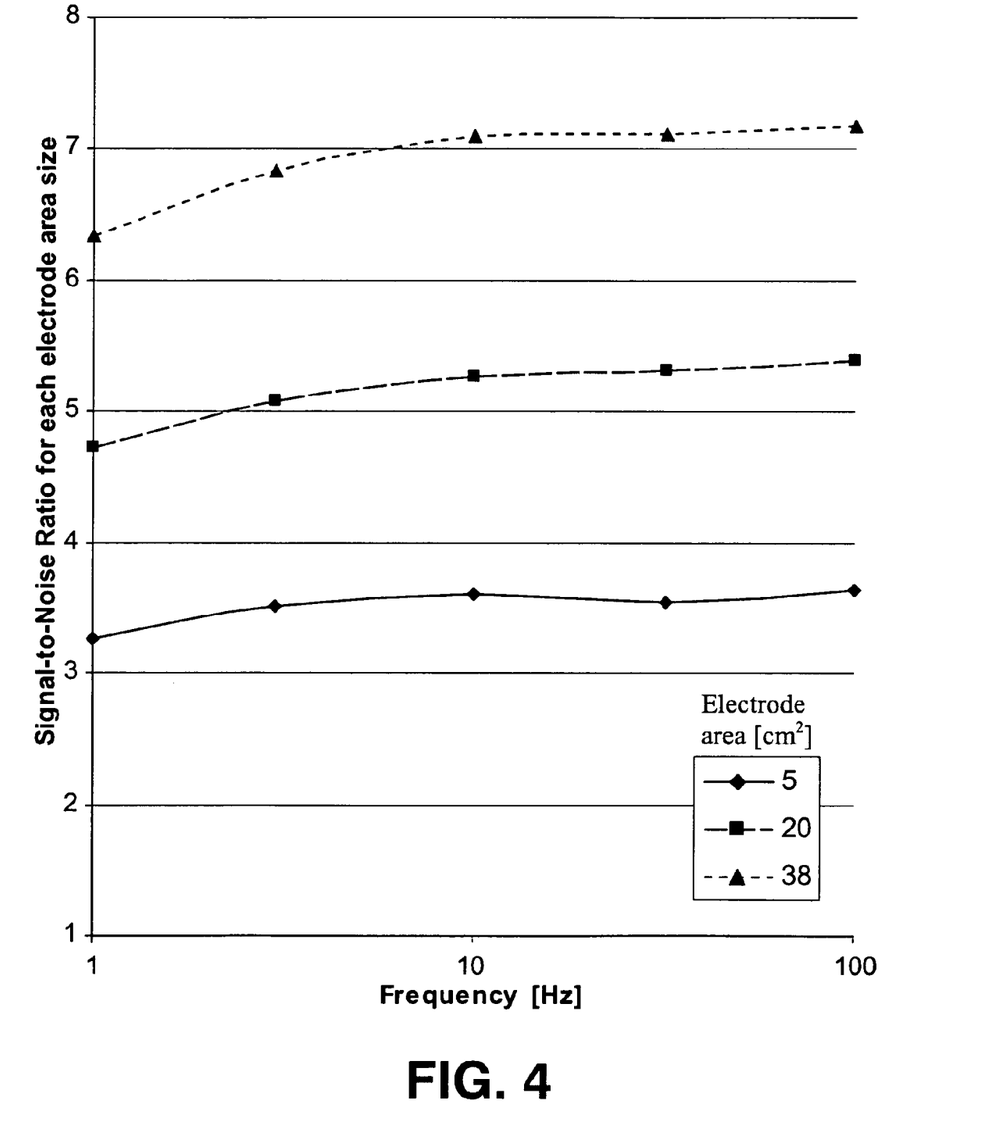
FIG. 4 is a graph of the Signal-to-Noise Ratio (SNR) for different electrode areas with signals of different frequencies.

Electrodes arrangements: there are some parameters to take into account in the design of the recording electrodes:

Area of the electrodes: the size of the electrode influences the quality of the obtained signal. Using the SNR as figure of merit, FIG. 4 shows how the quality of the registered signal (its SNR) increases when the area of the electrode increases. And this happens for all frequencies of the signal. As a matter of fact, there is an almost lineal relationship ($R^2>0.99$) between electrode area and SNR. Therefore, the bigger the area of the electrode, the higher quality the registered signal will have. As a drawback, bigger electrodes yield less spatial resolution, so information about where in the tank the animals' activity is taking place will be reduced.

Figure 5:
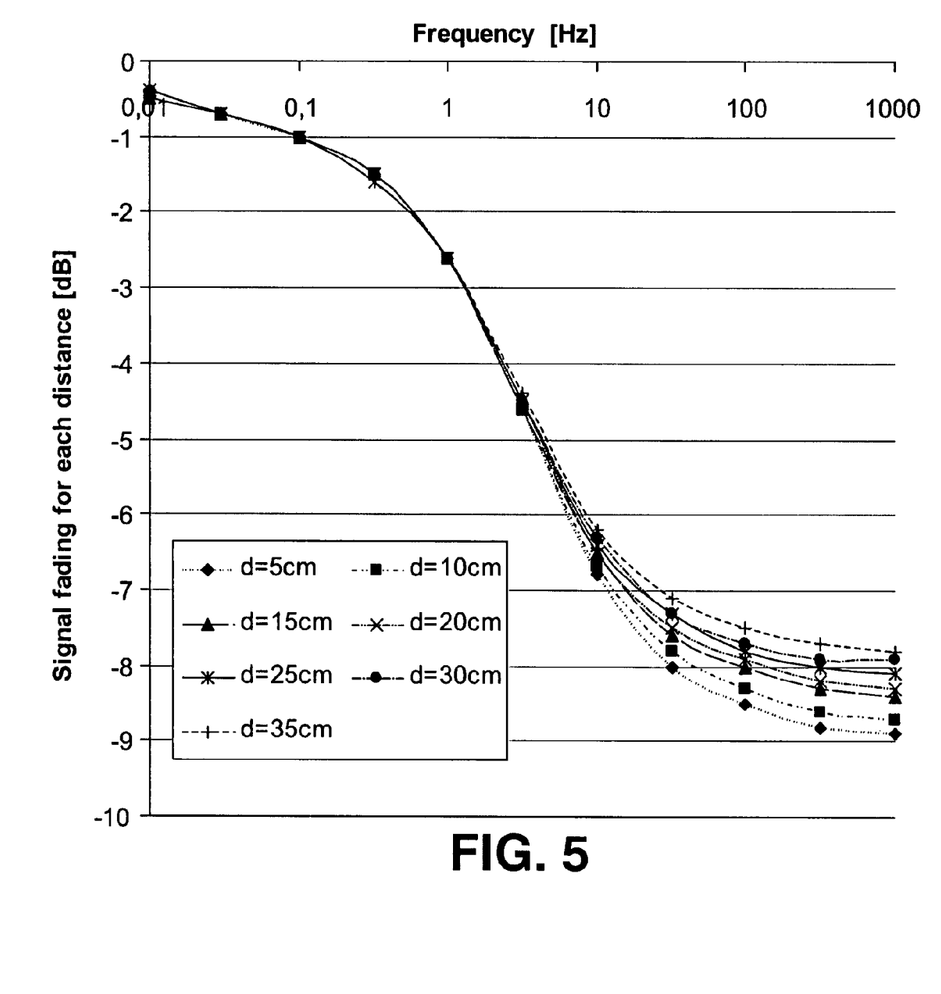
FIG. 5 is a graph showing the progressive fading of the signal (negative gain, measured in decibels) for higher frequencies.

Distance between signal source and electrode: this distance also influences the quality of the obtained signal as shown in FIG. 5. The progressive fading of the signal (as seen by its negative gain, measured in decibels—dB) due to the distance between signal source and recording electrode is however less important than the one suffered by higher frequencies. Numerically, for a copper electrode, there is an average difference in fading of less than 0.5 dB for a difference of 30 cm of distance. On the other hand, there is an average difference in fading of nearly 8 dB for a difference of 3 orders of magnitude in the frequency of the source signal. That difference in the fading is more dramatic in the lowest frequencies (up to 10 Hz), where the relationship is logarithmic. Therefore, depending on the size of the tank, these characteristics of the electrode+water combination have to be taken into account.

Bio-Amplifier

The bio amplifier is a very sensitive instrument able to detect and magnify the small biological signals produced by the activity of the animal/s (EMG, ECG, etc.) so that they can become of appreciable amplitude. Given the small entity of aquatic animal bio-signals, the use of this instrument is essential.

Micro-Processor

Once amplified, the signals are passed on to a microprocessor that is in charge of filtering and interpreting them.

Filtering of the Signals

Some of the problems that have not been considered in previous inventions are the fact that the presence of water in the system might affect the quality of the recordings and the fact that the level of noise might mask completely the bio-potential signals.

Figure 2:
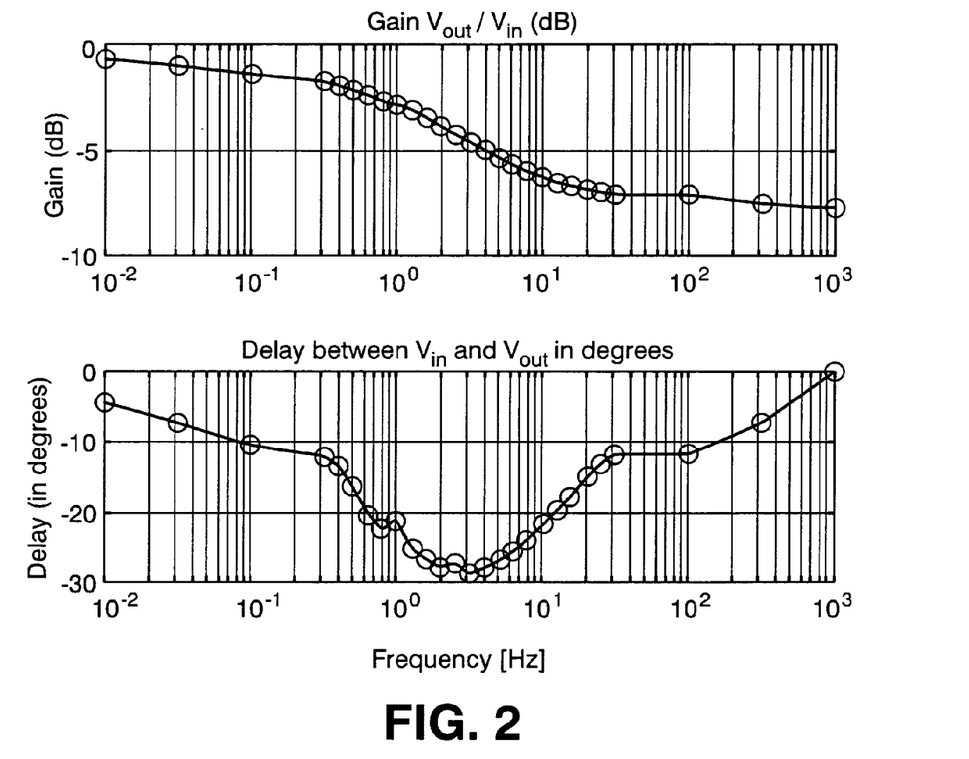
FIG. 2 is a Bode diagram of the water, which shows the different levels of fading produced by the water depending on the frequency of the signal.

Our results show that freshwater put in a water tank acts like a low pass filter. In other words, it acts like a filter that passes low-frequency signals but reduces considerably the amplitude of signals with frequencies higher than the cut-off frequency, which in this case is approximately 2 Hz; that is, the frequencies above 2 Hz are attenuated at least −3 dB (i.e., at least 1.000 times). See FIG. 2 in which a Bode diagram of the water is shown. The water fades away the high-frequency components of the signals produced by the aquatic animals, but the surrounding electromagnetic noise can reach the electrodes without crossing much volume of water, so the high-frequency components registered by the electrodes are surely just noise, not signals coming from the animals. That is the reason why low-pass filtering is so critical.

The electromagnetic noise encountered in measuring bio-potentials from aquatic animals was identified as white noise; a random signal with a flat power spectral density. In other words, the signal contains equal power within a fixed bandwidth at any centre frequency, except around the frequency of the mains (50 Hz in Europe).

A study was carried out to identify the frequency of the bio-potentials of aquatic animals. In fact, in order to develop a system able to detect animals' biological signals efficiently, it is necessary to identify in which bandwidth of frequency we need to filter to be able to eliminate the noise and retain the signal coming from the animals' activity. To this end, recordings with animals placed in a water tank were obtained and filtered using different band-pass filters (BP). The recorded signals were filtered by 11 different BP filters and the SNR was calculated for each bandwidth (from 10 to 1000 Hz). The results indicated that the highest SNR is located at the lowest frequencies, indicating that the signal produced by the animal (after crossing the water in the tank) was at the low frequencies. For this reason, a low-pass filter is essential to the invention. A band-pass filter from 0 Hz to 20 Hz is preferred, as it removes as much noise as possible from the recordings but at the same time retaining much of the original signal.

A low-pass filter is an electronic or software filter that allows to pass low-frequency signals, but attenuates (reduces the amplitude of) signals with frequencies higher than the cut-off frequency. A software low-pass filter can be implemented by, for example, an exponentially-weighted moving average, which is given by the following equation:

$$s_t = \sum_{n=1}^{k} w_n x_{t+1-n} = w_1 x_t + w_2 x_{t-1} + \ldots + w_k x_{t-k+1}.$$

$$\sum_{n=1}^{k} w_n = 1,$$

where $\{w_1, w_2, \ldots, w_k\}$ is a set of weighting factors such that x is the original signal, and s the signal filtered.

Figure 3:
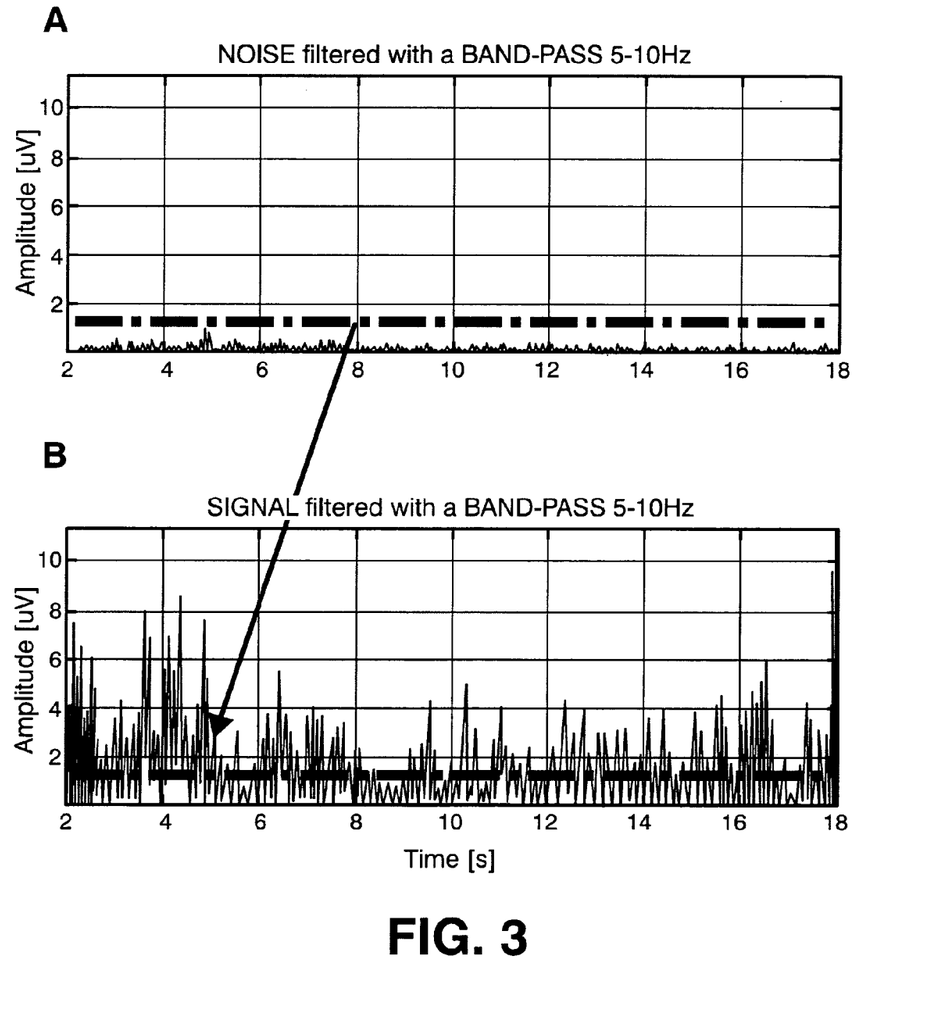
FIG. 3 is a diagram showing only Noise (A) and Signal+ Noise (B) filtered with a low pass filter to reduce the amplitude of the noise.

In our application, such a filter allows us to define a threshold, the amplitudes below which are considered as noise (see FIG. 3), and hence separating the target signal from background signal.

Interpretation of the Signal

The detected and processed signal is then correlated to the level of movement and activity of the animals by a scale ranged from 0 to 100% activity as follows:

For the 0%, a recording is made with the system with the tank full of water but with no animals in it. Therefore, this level corresponds to the amplitude of the electromagnetic noise present in the ambient.

For the 100%, a recording is made of several animals, one by one, very close to the electrodes in stressful conditions, so that the animal makes several and strong movements. The average of such recordings gives us an estimation of the maximum level of signal we can expect from an animal placed as close as possible to the electrode. Then, the scale is adjusted by multiplying that average by the amount of animals present in the tank at each time.

In addition, several other parameters are obtained from the signals provided by the electrodes, such as: where the animals spend more time (e.g., upper or lower part of the tank), whether there is a compact group of animals or several sub-groups, and whether there is a constant level of activity or if there are sudden peaks of activity, etc.

With those parameters, we create a "status vector" from which behavioural studies can be performed (including the measurement of the level of stress of the aquatic animals) using an automatic classifier trained with a wide set of signals by a human expert in the animals' behaviour.

Experiments and Corroborations

In order to verify whether the correspondence between the acquired biological signals and the animals movement was reliable, recordings with a webcam were carried out at the same time that the biopotentials of the animals were recorded with the system.

Figure 6A:
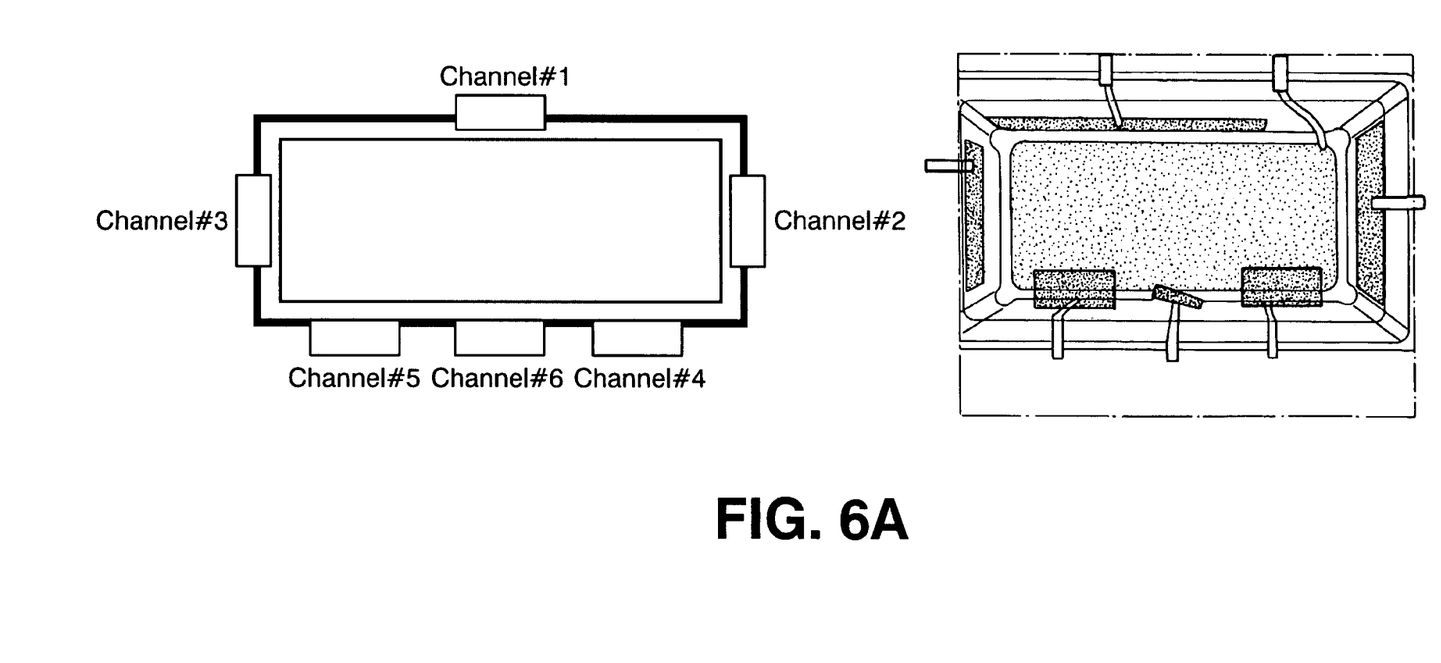
FIG. 6 is a graph showing a set-up (A) and correlation study between the signal acquired with the system and the one recorded by video (B).
Figure 6B:
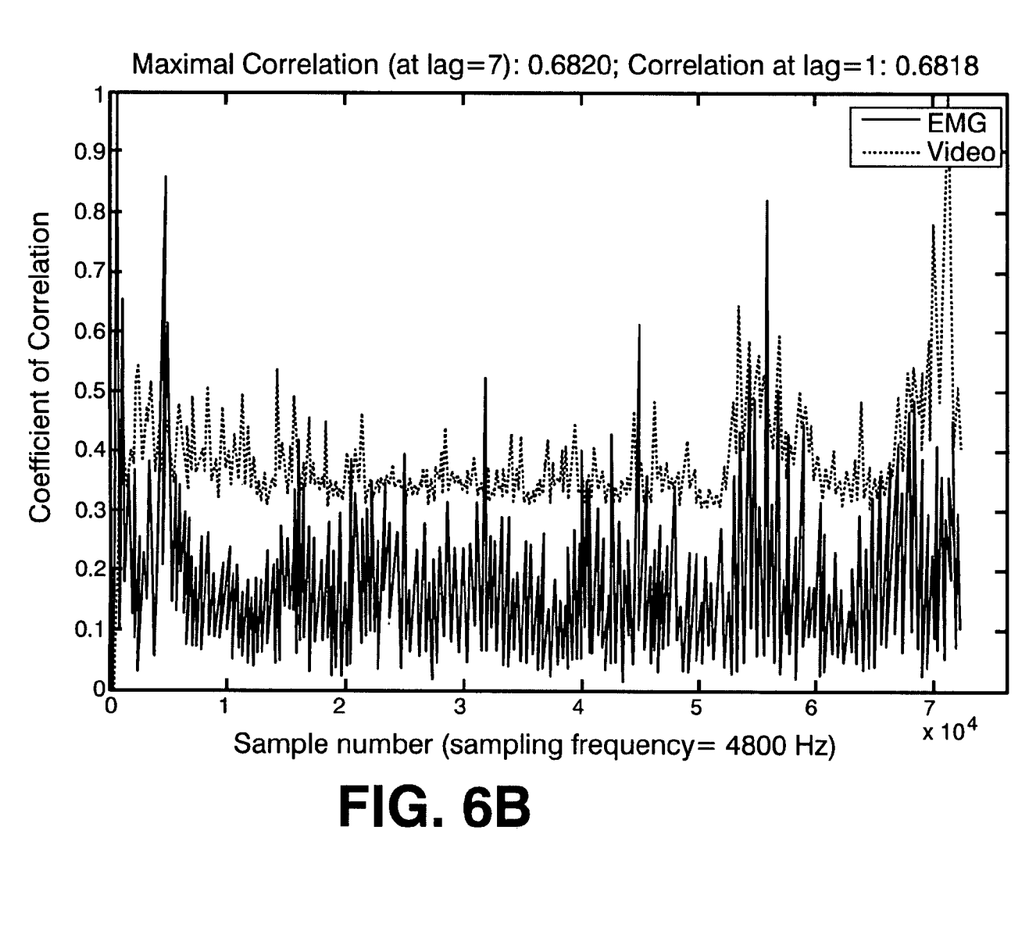

The high numerical correlation found between those two signals validated that the system effectively is able to detect animal activity through the evaluation of biological signals. See FIG. 6 for an example of that high correlation, where it can be seen that the same is, as usual, significant (>0.68).

In summary, the invention can provide a precise, quantifiable and specific indication of the level of stress/wellbeing of aquatic animals in normal living conditions as well as in experimental conditions without interfering with the animals life, as no electric current is applied to the animals, the signal detected is directly the signal produced by animal activity and the position of the electrodes does not interfere with the animals movements.

Therefore, signals acquired with the system of the invention can be used: i) for monitoring the animals' wellbeing status in laboratory experiments, in private houses (as a hobby); in restaurants showing edible aquatic animals such as fish and seafood in tanks; in aquaculture installations, etc.; ii) as an alternative/supportive approach to video-based systems in behavioural and neurological tests; and iii) to test the quality of the water (animal acting as a living sensor). Moreover, the signals acquired can be correlated to a specific scale indicating quantitatively the level of stress/wellbeing of the animals.

In this text, the term "comprises" and its derivations (such as "comprising", etc.) should not be understood in an excluding sense, that is, these terms should not be interpreted as excluding the possibility that what is described and defined may include further elements, steps, etc.

On the other hand, the invention is obviously not limited to the specific embodiment(s) described herein, but also encompasses any variations that may be considered by any person skilled in the art (for example, as regards the choice of materials, dimensions, components, configuration, etc.), within the general scope of the invention as defined in the claims.

The invention claimed is:

1. System for detecting the level of discomfort of aquatic animals during experimental studies, the system comprising:
    a water tank (1),
    a reference electrode (2) covering the entire surface of one of the sides of the tank in direct contact with the water, and
    an array of recording electrodes (3,3*a*,3*b*) in the form of printed circuit boards (PCB), covering the surface of another of the sides of the water tank, in direct contact with said side of the water tank,
    a bio amplifier (4) for amplifying a received bio-signal at the recording electrode,
    a micro-processor for treating the signals, and
    a low-pass filter for filtering the signals received, capable of filtering signals up to 20 Hz.

2. System according to claim 1 wherein the reference and signal electrodes (2, 3) are made of the same material.

3. System according to claim 2 wherein the electrodes are made of aluminum, copper or silver.

4. System according to claim 1, wherein the electrodes (2, 3 *a*, 3 *b* . . . ) are embedded in the walls of the tank (1).

* * * * *